(12) United States Patent
Zhang et al.

(10) Patent No.: US 8,927,603 B2
(45) Date of Patent: *Jan. 6, 2015

(54) X-RAY STERILIZATION OF LIQUID ADHESIVE COMPOSITIONS

(75) Inventors: Sheng Zhang, Hickory, NC (US); Rafael Ruiz, Sr., Hudson, NC (US)

(73) Assignee: Adhezion Biomedical, LLC, Wyomissing, PA (US)

( * ) Notice: Subject to any disclaimer, the term of this patent is extended or adjusted under 35 U.S.C. 154(b) by 62 days.

This patent is subject to a terminal disclaimer.

(21) Appl. No.: 13/154,524

(22) Filed: Jun. 7, 2011

(65) Prior Publication Data

US 2011/0318224 A1  Dec. 29, 2011

Related U.S. Application Data

(60) Provisional application No. 61/352,178, filed on Jun. 7, 2010.

(51) Int. Cl.
*A61K 31/275* (2006.01)
*A61L 2/08* (2006.01)

(52) U.S. Cl.
CPC .............. *A61L 2/082* (2013.01); *A61K 31/275* (2013.01)
USPC ........................................................ 514/526

(58) Field of Classification Search
None
See application file for complete search history.

(56) References Cited

U.S. PATENT DOCUMENTS

| | | | |
|---|---|---|---|
| 2,721,858 | A | 10/1955 | Joyner et al. |
| 3,254,111 | A | 5/1966 | Hawkins et al. |
| 3,527,224 | A | 9/1970 | Rabinowitz |
| 3,704,089 | A | 11/1972 | Stehlik |
| 5,530,037 | A | 6/1996 | McDonnell et al. |
| 5,874,044 | A | 2/1999 | Kotzev |
| 6,136,326 | A | 10/2000 | Kotzev |
| 6,143,805 | A | 11/2000 | Hickey et al. |
| 6,248,800 | B1 | 6/2001 | Greff et al. |
| 6,579,916 | B1 * | 6/2003 | Askill et al. ............... 522/152 |
| 6,738,451 | B2 | 5/2004 | Avnery |
| 2005/0047846 | A1 * | 3/2005 | Narang et al. ............ 401/133 |
| 2005/0197421 | A1 | 9/2005 | Loomis |
| 2006/0062687 | A1 | 3/2006 | Morales |
| 2007/0237296 | A1 | 10/2007 | Wyatt et al. |
| 2007/0248486 | A1 | 10/2007 | Morales |
| 2007/0261986 | A1 | 11/2007 | Bublewitz et al. |
| 2008/0021139 | A1 | 1/2008 | Blacklock et al. |
| 2008/0311323 | A1 | 12/2008 | Morales |
| 2009/0317353 | A1 | 12/2009 | Zhang et al. |
| 2009/0318583 | A1 | 12/2009 | Zhang et al. |

OTHER PUBLICATIONS

Silindir, M.; Ozer, A. Y. Sterilization Methods and the Comparison of E-Beam Sterilization with Gamma Radiation Sterilization. FABAD J. Pharm. Sci., 34, 43-53, 2009.*
Zhenghua, Y.; Yuesheng Li. Barrier property and structure of acrylonitrile/acrylic copolymers. Chinese Journal of Polymer Science, vol. 15, No. 3, pp. 236-241, 1997.*
Grégoire et al., "Radiological safety of medical devices sterilized with X-rays at 7.5 MeV" Radiation Physics and Chemistry 67 (2003) 149-167.
Sato et al., "Sterilization of Health Care Products by 5 MeV Bremsstrahlung (X ray)" Radiat. Phys. Chem. vol. 42, Nos. 4-6, pp. 621-624, 1993.
Croonenborghs, B., et al., "X-ray versus gamma irradiation effects on polymers", Radiation Physics and Chemistry, 76 (2007), pp. 1676-1678.
Hansen, "Food Irradiation and the Microwave/RF Market", Applied Microwave & Wireless, Feb. 2001, pp. 118-125.
Quinn, J.V., "Tissue Adhesives in Clinical Medicine", Second Ed., Chapter 3 (2005), BC Decker, Inc.
Canale, A.J., et al., "Methyl a-cyanoacrylate. I. Free-radical homopolymerization", J. Appl. Polym. Sci., 1960, 4:231-6 (Abstract).
Kaminski, A., et al., "Sterilisation by Irradiation", Essentials of Tissue Banking, Capter 9, 2010, p. 123-138.
Urena-Nune, F., et al., "Gamma Radiation-Polymerized Zn(II) Methacrylate as a Sorbent for Removal of Pb(II) from Wastewater", Ind. Eng. Chem. Res., 2007, 46, pp. 3382-3389.
Collinson, E., et al., "The y-Ray and X-Ray Induced Polymerization of Aqueous Solutions of Acrylonitrile", Discussions of the Faraday Society, 1952, 12:212-26.
Allcock, H.R., "X-Ray-Induced Polymerization of Diphenylvinylphosphine Oxide", J. Polymer Sci., 2:4087-95.
Grossoleil, J., et al., "X-Ray Induced Polymerization of Gaseous Vinyl Chloride, Effect of Additives", Canadian J. Chemistry, 49:363-70.

* cited by examiner

*Primary Examiner* — Robert A Wax
*Assistant Examiner* — Jessica Worsham
(74) *Attorney, Agent, or Firm* — Stradley Ronon Stevens & Young, LLP

(57) ABSTRACT

The invention provides a method of preparing a sterile, liquid adhesive composition in a sealed container using X-ray irradiation. The liquid adhesive compositions maintain their stability after sterilization and have an extended shelf life, making them particularly useful in the medical field.

20 Claims, No Drawings

X-RAY STERILIZATION OF LIQUID ADHESIVE COMPOSITIONS

CROSS-REFERENCE TO RELATED APPLICATIONS

This application claims the benefit of priority under 35 U.S.C. §119(e) to U.S. patent application Ser. No. 61/352,178, filed on Jun. 7, 2010, the disclosure of which is incorporated herein by reference in its entirety.

BACKGROUND OF THE INVENTION

1. Field of the Invention

The invention relates to methods of sterilizing liquid adhesive and microbial sealant compositions using X-ray irradiation. In particular, the invention relates to a method of sterilizing liquid adhesives in a sealed container at a dose of about 5 to about 40 kGy. In addition, the invention relates to a method of utilizing X-ray for the first time to sterilize liquid adhesive or microbial sealant compositions, which can provide an extended shelf life of at least two years after X-ray sterilization.

2. Description of the Prior Art

It is well-known that cyanoacrylate adhesives can be used for bonding tissue in surgical and medical procedures. In these applications, the adhesive composition can be used to close wounds, as well as to cover and protect surface injuries such as lacerations, abrasions, burns, sores and other open surface wounds. Additionally, liquid cyanoacrylate compositions recently have been found useful as liquid microbial sealant drapes to immobilize the bacteria before surgery. The cyanoacrylate adhesives are liquid monomers that polymerize on contact with tissue surfaces in an exothermic reaction creating a strong yet flexible film. This polymer film is generally formed rapidly. When cyanoacrylate adhesive compositions are used in the medical field, the adhesive compositions should be sterile. Several methods are known for sterilizing cyanoacrylate monomeric compositions.

Dry heat is one of the earliest sterilization methods used for sterilizing cyanoacrylate adhesives as disclosed in U.S. Pat. No. 5,874,044 to Kotzev; and U.S. Patent Application Publication Nos. 20080311323 and 20060062687 to Morales, which disclose using relatively lower temperatures. A disadvantage of dry heat sterilization is that the required temperatures can cause premature polymerization of the cyanoacrylate monomers.

Other known methods for sterilizing cyanoacrylate monomers include microwave sterilization, visible light sterilization and irradiation sterilization. Visible light sterilization is taught in U.S. Pat. No. 6,579,916 to Askill, wherein the disclosed method uses visible light irradiation having wavelengths of from 390 nanometers (nm) to 780 nm, at a dose of from about 0.01 to 50 joules/cm$^2$, at room temperature.

Electron beam (e-beam) irradiation sterilization is one of the most common methods for sterilizing cyanoacrylate compositions. U.S. Pat. No. 6,143,805 to Hickey et al. teaches sterilizing cyanoacrylate liquid adhesive compositions using e-beam irradiation which causes no substantial initiation of polymerization of the cyanoacrylate composition and results in compositions suitable for application to open wounds. U.S. Pat. No. 6,248,800 to Greff et al. discloses a method for sterilizing cyanoacrylate ester compositions using e-beam irradiation at room temperature, at a dose preferably from about 15 to 20 kGy, and a required average bulk density of the materials comprising the packaging element of less than about 0.2 gm/cm$^3$. U.S. Patent Application Publication No. 20070248486 discloses e-beam sterilization of cyanoacrylate ester compositions at doses as low as about 1 to about 5 kGy. A disadvantage to using e-beam irradiation for sterilizing cyanoacrylates is that it can also result in pre-mature polymerization of the monomers thus affecting both the shelf life and the performance of the product cyanoacrylate adhesives or sealants.

Gamma irradiation is yet another known method for sterilizing cyanoacrylate adhesives. U.S. Pat. No. 3,704,089 to Stehlik sterilizes cyanoacrylate adhesives by first freezing cyanoacrylate compositions into a solid state at very low temperatures (below −30° C.), then exposing them to gamma irradiation. U.S. Pat. No. 5,530,037 to McDonnell et al. teaches sterilizing cyanoacrylate adhesive compositions for medical use by using a minimum dose of 25 kGy gamma irradiation at room temperature. Such relatively high doses of aggressively penetrating gamma irradiation can easily cause changes in the formulated cyanoacrylate adhesive compositions resulting in unwanted and potentially harmful substances that negatively impact the ability of the adhesive to perform. Attempts to minimize these changes typically require the addition of very high levels of inhibitors, which can increase the toxicity of the mixture and increase the toxic by-products formed upon gamma irradiation. The use of high doses of toxic gamma irradiation to effect sterilization also raises safety concerns for workers who are exposed long term to this radiation.

Both gamma and electron beam irradiation sterilize medical products by destroying microorganisms with ionizing radiation. High energy X-rays, which are generated using high powered beams from electron accelerators, sterilize similarly with ionizing radiation. However, it is surprising that X-rays have never been used to sterilize cyanoacrylate compositions for medical use. This may partly be due to the fact that X-ray sterilization is historically still a young technology compared to processes using gamma and e-beam irradiation, which have been used for some time. Since first proposed about 40 years ago, X-ray sterilization of medical products has been investigated experimentally and theoretically by researchers and accelerator manufacturers. And while commercial use of X-ray sterilization began about 20 years ago, it has not been readily adopted due to the low output power of early X-ray generators and the known sensitivity of cyanoacrylates to irradiation which induces premature polymerization.

X-rays have many advantages over gamma and electron beam irradiation. X-rays are short-wavelength, high-frequency electromagnetic photons, which are emitted by high-energy electrons when they are deflected by atomic nuclei. X-rays at 5 MeV (million electron volts) and 7 MeV provide a greater penetration property than gamma irradiation from a cobalt-60 source. Gamma irradiations are emitted in all directions from a cobalt source, while x-rays are concentrated in the direction of the incident electron beam. The high intensity in the forward direction improves the efficiency of x-ray. High-energy X-rays are ideal for sterilizing large packages of medical devices and provide excellent dose uniformity while treating full pallets of medical devices compared to gamma sterilization. X-rays are generated by a machine, while cobalt producing reactors of gamma rays will require expensive upgrades in the coming years. Compared to gamma irradiation, X-ray sterilization does not require radioactive transport or waste management. Based on the regulatory rules, transportation of radioactive cobalt-60 is presently challenging and relevant regulations are generated more and more every year. The flexibility of X-rays is another compelling reason to use this sterilization method for medical devices. Compared to gamma, X-rays adapt better to changing volumes of materials to be sterilized. Source loading of gamma rays is prepared by detailed calculations, which is fixed and very difficult to modify, while x-ray beam configurations can be changed by simply a mouse click. In addition, X-ray sterilization induces a small temperature variation which does not damage plastic materials, often used to contain the compositions.

High-power and high-energy X-ray accelerators have recently been developed, which facilitate the industrial and medical application of X-ray sterilization. U.S. Pat. No. 6,738,451 to Avnery discloses an apparatus used for sterilizing medical instruments more quickly and thoroughly. The X-ray beam emitter includes a vacuum chamber having a target window. An electron generator is positioned within the vacuum chamber for generating electrons to form X-rays. U.S. Patent Application Publication No. 20070237296 to Wyatt et al. discloses a sterilization device that consists of at least one planar X-ray source and an irradiation chamber which receives X-rays. The planar x-ray source is composed of an electron target that receives electrons from the cathode, a field emission cathode and an applied voltage for accelerating electrons from the cathode to the target. While the early unit costs of X-ray sterilization may be comparable to other treatment methods, in the long term, X-ray sterilization will be more cost effective.

The US Food and Drug Administration (FDA) has approved food irradiation with X-ray energies up to 7.5 MeV. Lately, x-rays have been extensively used to sterilize large quantities of mail. U.S. Patent Application Publication No. 20070261986 to Bublewitz et al. discloses a method for sterilizing medical single-component or multi-component impression materials. The components of the impression materials are contained into a primary package, which are sterilized by heat sterilization. The sterilized components in the primary package are introduced into a secondary package, which are then sterilized by a suitable gas sterilization, or irradiation sterilization such as x-ray sterilization. X-ray has been investigated to sterilize health care products. Radiation sensitivities and the dose rate effects of *B. pumilus* and *B. subtilis* were examined for x-rays and cobalt-60 gamma rays. Compared to gamma sterilization, the results provided the supporting data for possible sterilization of medical devices by x-rays (Sato et al. *Radia. Phys. Chem.* 42, 621-624, 1993). Additionally, radiological safety of medical devices sterilized with x-rays at 7.5 MeV was investigated by Gregoire et al. who concluded that sterilization with X-rays at 7.5 MeV can be considered safe from the standpoint of public health and personal safety if certain precautions are taken (Gregoire et al. *Radia. Phys. Chem.* 67, 149-167, 2003).

In spite of the fact that X-rays have been proposed for sterilizing food and medical devices, X-rays have never been used to sterilize cyanoacrylate adhesive and microbial sealant compositions. Compared to gamma and e-beam sterilization, X-ray irradiation provides the many advantages as described above. It would be advantageous and beneficial to the industry to provide an x-ray irradiation method of sterilizing cyanoacrylate compositions. Therefore, it is an object of the present invention to apply X-ray irradiation for the first time to sterilize cyanoacrylate monomer compositions, which have a useful extended shelf life, making them particularly suitable for medical applications.

SUMMARY OF THE INVENTION

The present invention is directed to a method of sterilizing liquid adhesive and/or microbial sealant compositions. In particular, the present invention provides for a method of sterilizing liquid adhesive or microbial sealant compositions using X-ray sterilization. Liquid adhesives and microbial sealants sterilized by the inventive method provide adhesive products which in addition to being sterile, exhibit substantially no polymerization after sterilization, are stable and have extended shelf lives making them suitable for medical use.

The novel method of the instant invention utilizes X-ray irradiation at doses, including the range of about 5 kGy to about 40 kGy, preferably about 5 kGy to about 30 kGy, more preferably in the range of about 5 kGy to about 25 kGy, and even more preferably in the range of about 10 kGy to about 20 kGy. In a preferred embodiment, the dose range of X-ray irradiation can be as low as about 5-8 kGy to sufficiently sterilize the liquid adhesive or microbial sealant compositions. The present invention is directed to a method for preparing a sterile, liquid adhesive composition in a container using X-ray irradiation wherein the method comprises:
  (1) stabilizing a liquid adhesive composition using a combination of a free radical and an anionic stabilizer to produce a stabilized composition;
  (2) placing the stabilized liquid adhesive composition in a container and sealing said container; and
  (3) irradiating the stabilized liquid adhesive composition in said sealed container with X-ray irradiation at a dose of from about 5 kGy to about 40 kGy.

The liquid adhesive compositions exhibit good shelf stability after X-ray sterilization. The accelerated aging tests at 80° C. for 13 days confirmed an extended shelf life of at least 2 years of the liquid adhesive or microbial compositions sterilized by X-ray irradiation. In preferred embodiments, X-ray irradiation induces essentially no change in viscosity of the liquid adhesive compositions, indicating that almost no substantial pre-mature polymerization of the liquid adhesives or sealants occurs upon X-ray irradiation.

DETAILED DESCRIPTION OF THE PREFERRED EMBODIMENTS

The present invention is directed to a method of sterilizing a liquid adhesive or microbial sealant compositions in a container using X-ray irradiation. As used herein, the term "adhesive" or "adhesives" includes sealant or sealants, particularly microbial sealants. In certain embodiments, the liquid adhesive composition, packaged in a container, is subjected to a dose of 5 kGy to 40 kGy, preferably in the range of about 5 kGy to 30 kGy, more preferably about 5 kGy to 25 kGy, and most preferably about 10 kGy to 20 kGy.

The method is one comprising: (1) providing stable adhesive compositions comprising a combination of desirable free radical and anionic stabilizers and incorporating desirable or suitable additives such as polymerization one or more of an accelerator, thickener, strength enhancer, colorant, plasticizer and others; (2) packaging the cyanoacrylate adhesive in a container; and (3) sterilizing the adhesive or microbial sealant composition with X-ray irradiation at a preferred dosage of 5 kGy-25 kGy.

The adhesive compositions sterilized by X-ray irradiation of the present invention may be any adhesive for industrial, home, commercial or medical use. Preferred adhesives are those suitable for medical use. As medical adhesives, compositions sterilized by the instant method find a variety of uses, including for inhibiting bleeding, closing surgical wounds, dressing burns, covering damaged and/or lacerated tissues, covering bedsores and/or other open wounds.

Sterilized compositions finding use as microbial sealants may be applied over a surgical site before surgery to prevent surgical site infection. Microbial sealant compositions provide a thin and uniform film on the surgical sites to form a "drape", and in preferred embodiments, has a thickness of from about 5 to about 600 μm. More preferably, the drape film provides a thickness of about 10 to 500 μm, more preferably from about 30 to 300 μm and still more preferably from about 40 to 200 μm. The liquid microbial sealants can overcome the challenges and problems associated with conventional surgical incise drapes. The lifting of the conventional surgical incise drapes at the end of a surgical procedure may result in bacteria entering the surgical site, while the liquid microbial sealant can form a tight microbial sealant on the surgical site. At removal of the conventional surgical incise drape with strong adhesion strength, the upper layer of the skin may come away with the draping, leading to skin damage. Removal of a liquid microbial sealant is not necessary because it sloughs off as the skin regenerates. A microbial sealant film can slough off anywhere within about 3 to about 10 days. Non-adherence or wrinkling of the conventional surgical incise drapes can result in failure to prevent the microorganisms from entering into the surgical site, while liquid microbial sealants can provide a flexible sealant with a desired bonding strength. The conventional surgical incise drape cannot provide post-surgery infection prevention because of its removal after the surgical procedure, while microbial sealant composition can stay on the surgical site for a few days providing post-surgery antimicrobial characteristics.

High energy electrons are used in the instant method of x-ray sterilization of liquid adhesive compositions. X-rays are generated as high-frequency and short-wavelength electromagnetic photons. Conventional x-ray technology is suitable in the instant invention. The X-ray energy used in the present invention ranges from 1 million to 10 million electron volts (MeV), preferably 3 MeV to 10 MeV, and more preferably 3 to 7.5 MeV. X-ray power can be increased drastically by increasing the electron energy and the x-ray current. The current used in the present invention ranges from about 10 to 150 milliamperes (mA), preferably about 10 to 100 mA, and more preferably about 15 to 100 mA.

The source used to generate X-rays is referred to as the X-ray target. Conventional X-ray targets are suitable in the instant invention such as an elongated X-ray target comprising a thin sheet of tantalum. The thickness of a sheet of tantalum may be in the range of about 0.05 mm to about 5 mm, preferably about 0.05 mm to about 5 mm, and more preferably about 0.1 mm to 3 mm. The thin sheet of tantalum can be cooled with for example, a fast-flowing stream of water. The water stream may have a thickness of about 1 mm to about 20 mm, preferably of about 1 mm to about 15 mm, and more preferably of about 1 mm to about 10 mm. Typically the water stream is confined by a thin sheet of stainless steel with a thickness of about 0.03 mm to about 6 mm, preferably about 0.05 mm to about 4 mm, and more preferably about 0.05 mm to 2.5 mm. The total thickness of the X-ray target assembly is desirably greater than the maximum range of the primary electrons so that said liquid adhesive or microbial sealant compositions are not irradiated by the electron beam but only by the X-rays emitted from the target.

The width of the scanned electron beam is suitably from about 20 cm to about 500 cm, preferably from about 30 cm to about 400 cm, and more preferably from about 40 cm to about 300 cm. The distance from the x-ray target to the sealed container of liquid adhesive composition is desirably from about 10 cm to about 400 cm, preferably from about 20 cm to 350 cm, and more preferably from about 30 cm to 300 cm.

In order to reduce the bioburden, the liquid monomeric adhesive or microbial sealant compositions in the present invention may be filtered by at least one filtration step under an inert and moisture-free atmosphere such as medical grade nitrogen prior to X-ray sterilization. This step functions to reduce the bioburden of the cyanoacrylate adhesive composition prior to X-ray sterilization according to the present invention. The at least one filter preferably has a pore size of from about 1 to about 200 micrometers, more preferably from about 1 to about 100 micrometers, and even more preferably from about 2 to about 50 micrometers. The second and additional filters preferably have a pore size of from about 0.01 to about 10 micrometers, more preferably from about 0.05 to about 10 micrometers, and even more preferably from about 0.05 to about 2 micrometers. Medical grade nitrogen, for example, has a purity of at least 99%, preferably 99.5% and more preferably 99.8%. The container that includes liquid monomeric adhesive or microbial sealant compositions may also be sanitized with ethylene oxide prior to the final x-ray sterilization.

According to the embodiments of the present invention, a sterility assurance level (SAL) should be obtained at a minimum of $10^{-3}$, which means that the probability of a single unit being non-sterile after sterilization is 1 in 1000. In embodiments, sterility assurance level may be at least $10^{-4}$, or may be at least $10^{-5}$, or may be at least $10^{-6}$.

According to the embodiments of the present invention, "sterilization" means inactivation of viruses, bacteriophages, or viable microorganisms such as bacteria and fungi, the activity that effectively kills or eliminates transmissible agents such as bacteria, fungi, viruses, or spore forms from various substrates or biological culture mediums, or the reduction to an acceptable level of viable organisms, viruses or bacteriophages. The acceptable level is a level at which, the particular viable organisms, bacteriophages, or viruses cannot be detectable in said sterile liquid adhesive or microbial sealant composition. Tests for fungal and bacterial contamination are well known in the art, which are carried out on different culture media such as soybean casein digest medium, fluid thioglycollate medium, tryptose phosphate broth, tryptic soy broth, blood agar plates, sabouraud agar plates, and nutrient agar. The sterility of the liquid adhesive or microbial sealant compositions sterilized by X-ray irradiation was analyzed by Bacteriostasis and Fungistasis tests in culture media. Culture media can be assessed for active growth. After testing with challenging microorganisms such as *Bacillus subtilis, Candida albicans*, or *Aspergillus niger*, no growth of the microorganisms was observed, indicative of the sterility of the cyanoacrylate adhesive or microbial sealant compositions sterilized by X-ray irradiation.

According to the embodiments of the present invention, liquid adhesive compositions in a sealed container were irradiated by x-ray radiation in a stationary position under the x-ray target and at different doses. The viscosity of the liquid adhesive compositions was measured before and after x-ray sterilization by a Brookfield DV-II+ viscometer. About 0.5 ml of a said composition was put into the cup and the cup was brought into position and slowly secured with the retaining arm. The motor was turned on after the sample was equilibrated in the cup. The viscosity of the compositions was measured in triplicate. The spindle and cup were cleaned with acetone after each measurement.

It has surprisingly been found that x-ray sterilization of liquid adhesive compositions results in almost no change in viscosity of the compositions, indicating that no pre-mature polymerization of the compositions occurs upon x-ray sterilization. Furthermore, the liquid monomer adhesive or microbial sealant compositions provide an extended shelf life of at least two years.

Table A summarizes the viscosity of different cyanoacrylate compositions before and after sterilization by X-ray at various dose ranges. Upon X-ray irradiation, the viscosity of various cyanoacrylate compositions only slightly decreases or increases and the variation of viscosity upon x-ray sterilization is within the measurement error of the viscometer. As shown in Table A, the average viscosity of composition 1b changes from 7.56 centipoise (cps) before x-ray sterilization to 7.77 cps, 6.95 cps, and 6.54 cps after X-ray sterilization at dose ranges 6.96-8.59 kGy, 11.89-13.69 kGy, and 15.25-18.88 kGy, respectively.

TABLE A

Viscosity of liquid monomeric adhesive or microbial sealant compositions before and after X-ray sterilization at different dosage ranges

| Sample | Dosage range (kGy) | Before X-ray irradiation | | | | After X-ray irradiation | | | |
|---|---|---|---|---|---|---|---|---|---|
| | | 1 | 2 | 3 | average | 1 | 2 | 3 | average |
| 1a | 6.96-8.59 | 6.74 | 6.74 | 7.36 | 6.95 | 6.13 | 6.13 | 7.36 | 6.54 |
| | 11.89-13.69 | | | | | 6.13 | 6.13 | 7.36 | 6.54 |
| | 15.25-18.88 | | | | | 6.74 | 7.36 | 7.97 | 7.36 |
| 1b | 6.96-8.59 | 7.97 | 7.97 | 6.74 | 7.56 | 7.36 | 7.97 | 7.97 | 7.77 |
| | 11.89-13.69 | | | | | 6.74 | 7.36 | 6.74 | 6.95 |
| | 15.25-18.88 | | | | | 6.74 | 6.74 | 6.13 | 6.54 |
| 1c | 6.96-8.59 | 7.36 | 6.13 | 6.74 | 6.74 | 7.36 | 6.74 | 7.36 | 7.15 |
| | 11.89-13.69 | | | | | 7.36 | 7.97 | 6.74 | 7.36 |
| | 15.25-18.88 | | | | | 7.36 | 7.97 | 7.97 | 7.77 |
| 1d | 6.96-8.59 | 7.97 | 7.97 | 7.36 | 7.77 | 6.13 | 6.13 | 6.13 | 6.13 |
| | 11.89-13.69 | | | | | 7.36 | 6.13 | 6.13 | 6.54 |
| | 15.25-18.88 | | | | | 6.74 | 7.36 | 7.97 | 7.36 |

It is an advantage of the present invention that the integrity of the adhesive composition is maintained upon X-ray sterilization, as confirmed by no or negligible change in viscosity after X-ray irradiation. It has been reported by others that the viscosity of cyanoacrylate compositions often changes after sterilization. Cyanoacrylate adhesives reported in the prior art demonstrated a dramatic increase in viscosity induced by sterilization, as reported by Rabinowitz in U.S. Pat. No. 3,527,224. And in fact, sterilization is often used to intentionally increase the viscosity of cyanoacrylate adhesives. The compositions and methods of the present invention minimize the variation in viscosity of cyanoacrylate adhesives due to sterilization.

According to preferred embodiments of the present invention, the liquid adhesive compositions after X-ray sterilization provide a stable shelf life for use in the medical field. The shelf life stability of liquid adhesive compositions sterilized by x-ray irradiation was evaluated by an accelerated aging study at 80° C. The study was performed in an oven at 80° C. for a period of 13 days. The investigated compositions were tested for viscosity at intervals of 0, 6, and 13 days. Based on ASTM F19802, 13 days accelerated aging at 80° C. correlates to 2 years of shelf life at ambient temperatures and 1 day of accelerated aging at 80° C. is equal to 56 days.

The viscosity of the cyanoacrylate compositions after x-ray sterilization at different dosage levels increased as the accelerated aging proceeded but the viscosity of the aged sample after day 13 is within an acceptable range, as shown in the following Table B. The aged samples at day 13 at 80° C. does not affect the wound closure properties of adhesives, the antimicrobial property of microbial sealants or the ability to dispense the compositions from the applicator. For example, the average viscosity of the cyanoacrylate adhesive composition sterilized by x-ray irradiation at 11.89-13.69 kGy, at accelerated aging day 0, day 6, and day 13 was 6.54 cps, 8.99 cps, and 19.63 cps, respectively. The accelerated aging study indicates that the cyanoacrylate adhesive compositions sterilized by X-ray irradiation demonstrate a shelf life of at least two years.

TABLE B

The viscosity of cyanoacrylate-based composition (1a) sterilized by X-ray at different dose ranges, at different intervals of the accelerated aging at 80° C.

| Dosage range (kGy) | Average viscosity (cps) at different intervals of the accelerated aging at 80° C. | | |
|---|---|---|---|
| | Day 0 | Day 6 | Day 13 |
| 6.96-8.59 | 6.54 | 8.58 | 9.19 |
| 11.89-13.69 | 6.54 | 8.99 | 19.63 |
| 15.25-18.88 | 7.36 | 9.60 | 44.77 |

In preferred embodiments of the present invention, the cyanoacrylate monomers can be prepared according to methods known in the art. Reference is made, for example, to U.S. Pat. Nos. 2,721,858 and 3,254,111, each of which is hereby incorporated in its entirety by reference. One such process includes, for example, reacting a cyanoacetate with formaldehyde in the presence of a basic condensation catalyst at an elevated temperature to produce a low molecular weight polymer. A de-polymerization (or cracking) step is followed under high temperature and high vacuum in the presence of acidic and anionic inhibitors, yielding a crude monomer that can be distilled under high temperature and high vacuum in the presence of radical and acidic inhibitors.

In a preferred embodiment, the adhesive compositions of the present invention are based upon one or more polymerizable cyanoacrylate monomers, and/or reactive oliogmers of cyanoacrylate. Such cyanoacrylate monomers are readily polymerizable, e.g., anionically polymerizable or free radical polymerizable, to form polymers. Cyanoacrylate monomers suitable for use in accordance with the present invention include, but are not limited to, 1,1-disubstituted ethylene monomers of the formula:

$$HRC=CXY \qquad (I)$$

wherein X and Y are each strong electron withdrawing groups, and R is H, $-CH=CH_2$, or a $C_1$-$C_4$ alkyl group. Examples of monomers within the scope of formula (I) include alpha-cyanoacrylates, vinylidene cyanides, $C_1$-$C_4$ alkyl homologues of vinylidene cyanides, dialkyl methylene malonates, acylacrylonitriles, vinyl sulfinates and vinyl sulfonates of the formula $CH_2=CX'Y$ wherein X' is $-SO_2R'$ or —SO₃R' and Y' is —CN, —COOR', —COCH₃, —SO₂R' or —SO₃R', and R' is H or hydrocarbyl. Preferred monomers of formula (I) for use in this invention are alpha-cyanoacrylates. These monomers are known in the art and have the formula:

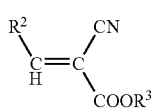
(II)

wherein R² is hydrogen and R³ is a hydrocarbyl or substituted hydrocarbyl group; a group having the formula —R⁴—O—R⁵—O—R⁶, wherein R⁴ is a 1,2-alkylene group having 2-4 carbon atoms, R⁵ is an alkylene group having 2-12 carbon atoms, and R⁶ is an alkyl group having 1-6 carbon atoms; or a group having the formula:

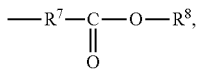

wherein R⁷ is:

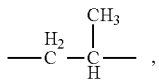

or —[C(CH₃)₂]ₙ—
wherein n is 1-14, preferably 1-8 carbon atoms and R⁸ is an organic moiety.

Examples of suitable hydrocarbyl and substituted hydrocarbyl groups include straight chain or branched chain alkyl groups having 1-16 carbon atoms; straight chain or branched chain C₁-C₁₆ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms cycloalkyl groups; arylalkyl groups; alkylaryl groups; and aryl groups.

The organic moiety R⁸ may be substituted or unsubstituted and may be a straight chain, branched or cyclic, saturated, unsaturated or aromatic. Examples of such organic moieties include C₁-C₈ alkyl moieties, C₂-C₈ alkenyl moieties, C₂-C₈ alkynyl moieties, C₃-C₁₂ cycloaliphatic moieties, aryl moieties such as phenyl and substituted phenyl, and arylalkyl moieties such as benzyl, methylbenzyl and phenylethyl. Other organic moieties include substituted hydrocarbon moieties, such as halo (e.g., chloro-, fluoro- and bromo-substituted hydrocarbons) and oxy- (e.g., alkoxy substituted hydrocarbons) substituted hydrocarbon moieties. Preferred organic radicals are alkyl, alkenyl and alkynyl moieties having from 1 to about 8 carbon atoms, and halo-substituted derivatives thereof. Particularly preferred are alkyl moieties of 4 to 8 carbon atoms. In the cyanoacrylate monomer of formula (II), R³ is preferably an alkyl group having 1-10 carbon atoms or a group having the formula -AOR⁹, wherein A is a divalent straight or branched chain alkylene or oxyalkylene moiety having 2-8 carbon atoms, and R⁹ is a straight or branched alkyl moiety having 1-8 carbon atoms. The preferred alpha-cyanoacrylate monomers used in this invention are 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate, or a combination thereof.

In embodiments of the present invention, the liquid monomer adhesive compositions are stabilized by using a combination of free radical and anionic stabilizers. The stabilizers may be present in an amount of 200 ppm to 1500 ppm, preferably 1000 ppm to 10000 ppm, and more preferably 2000 ppm to 8000 ppm. The preferred free radical stabilizer is butylated hydroxy anisole (BHA). Suitable free radical stabilizers include without limitation; butylated hydroxy anisole (BHA); hydroquinone; catechol; hydroquinone monomethyl ether and hindered phenols such as butylated hydroxyanisol; 4-ethoxyphenol; butylated hydroxytoluene (BHT, 2,6-di-tert-butyl butylphenol), 4-methoxyphenol (MP); 3-methoxyphenol; 2-tert-butyl-4-methoxyphenol; and 2,2-methylene-bis-(4-methyl-6-tert-butylphenol). The preferred stabilizer is BHA.

According to embodiments of the present invention, the preferred anionic stabilizer is sulfur dioxide in an amount of about 2 ppm to about 500 ppm, preferably about 10 ppm to about 200 ppm. Other anionic stabilizers may be a very strong acid including without limitation perchloric acid, hydrochloric acid, hydrobromic acid, toluenesulfonic acid, fluorosulfonic acid, phosphoric acid, ortho, meta, or para-phosphoric acid, trichloroacetic acid, and sulfuric acid. The very strong acid is used in an amount of about 1 ppm to about 250 ppm, preferably from about 5 ppm to about 50 ppm.

In preferred embodiments of the present invention, a polymerization accelerator may be included in the liquid monomeric adhesive compositions sterilized by X-ray irradiation. Suitable polymerization accelerators may be selected from calixarenes and oxacalixarenes, silacrowns, crownethers, cyclodextrin and its derivatives, polyethers, aliphatic alcohol, various aliphatic carboxylic acid esters, benzoyl peroxide, amine compounds such as are triethyl amine, diethyl amine, butyl amine, isopropyl amine, tributyl amine, N,N,-dimethyl aniline, N,N-diethyl aniline, N,N-dimethyl-p-toluidine, N,N-dimethyl-m-toluidine, N,Ndimethyl-o-toluidine, dimethyl benzyl amine, pyridine, picoline, vinyl pyridine, ethanolamine, propanolamine and ethylene diamine, quaternary ammonium salts such as alkyl ammonium salts, amide-bonded ammonium salts, ester-bonded ammonium salts, ether-bonded ammonium salts and alkylimidazolinium salts, cyclosulfur compounds and derivatives, and polyalkylene oxides and derivatives.

In preferred embodiments of the present invention, a crown ether as the accelerator may be included in the liquid monomeric adhesive or sealant compositions sterilized by X-ray irradiation at lower dose levels. Examples of crown ether include, but are not limited to, 15-crown-5, 18crown-6, dibenzo-18-crown-6, tribenzo-18-crown-6, dicyclohexyl-18-crown-6, benzo-15-crown5, dibenzo-24-crown-8, dibenzo-30-crown-10, asym-dibenzo-22-crown-6, dimethylsila-11 crown-4, dimethylsila-14-crown-5, dimethylsila-17-crown-6, dibenzo-14-crown-4, dicyclohexyl24-crown-8, asym-dibenzo-22-crown-6, cyclohexyl-12-crown-4, 1,2-decalyl-15-crown-5, 1,2naphtho-15-crown-5, 3,4,5-naphthyl-16-crown-5, 1,2-methyl-benzo-18-crown-6, 1,2-methylbenzo-5, 6-methylbenzo-18-crown-6, 1,2-t-butyl-18-crown-6, 1,2-vinylbenzo-15-crown-5, 1,2-vinylbenzo-18-crown-6, 1,2-t-butyl-cyclohexyl-18-crown-6, and 1,2-benzo-1,4-benzo-5oxygen-20-crown-7.

The amount of polymerization accelerator that is added to the liquid adhesive composition is in the amount of about 10 ppm-6000 ppm. In preferred embodiments, the polymerization accelerator is present in the amount of about 40 ppm-5000 ppm, and more preferably about 60 ppm-4000 ppm of the liquid adhesive composition. The amount of polymerization accelerator to be use can be determined by one of ordinary skill in the art using known techniques without undue experimentation.

In embodiments, the adhesive compositions may optionally include at least one plasticizing agent that imparts flexibility to the polymer formed from the monomer. The plasticizing agent preferably does not contain any moisture and should not adversely affect the stability of said cyanoacrylate compositions. Examples of suitable plasticizers include, but are not limited to, tributyl citrate (TBC), acetyl tributyl citrate (ATBC), dimethyl sebacate, diethylsebacate, triethyl phosphate, tri(2-ethyl-hexyl)phosphate, tri(p-cresyl)phosphate, diisodecyl adipate (DIDA), glyceryl triacetate, glyceryl tributyrate, dioctyl adipate (DICA), isopropyl myrisate, butyl sterate, lauric acid, trioctyl trimelliate, dioctyl glutatrate (DICG) and mixtures thereof. Tributyl citrate, diisodecyl adipate and acetyl tributyl citrate are preferred plasticizers, which when present are in an amount of up to thirty percent (30%) by weight of the liquid adhesive composition The amount to be used can be determined by one of ordinary skills in the art, using known techniques without undue experimentation.

The liquid adhesive compositions sterilized by x-ray irradiation may optionally contain thickening agents. Suitable thickening agents include, but are not limited to, polycaprolactone, copolymers of alkylacrylate and vinyl acetate, polyalkyl methacrylates, polyalkyl acrylates, lactic-glycolic acid copolymers, lactic acid-caprolactone copolymers, polyorthoesters, copolymers of alkyl methacrylates and butadiene, polyoxalates, and triblock copolymers of polyoxypropylene flanked by two hydrophilic chains of polyoxyethylene. Preferred thickening agents include a partial polymer of cyanoacrylate as disclosed in U.S. patent application Ser. No. 12/214,791, and triblock copolymers of polyoxyalkylene as disclosed in U.S. patent application Ser. No. 12/214,794. Preferably the thickening agent is miscible in cyanoacrylate monomer compositions at room temperature.

According to the embodiments of the present invention, the liquid adhesive compositions containing a thickening agent have a viscosity such that the liquid composition stops flowing beyond the intended application site or is substantially prevented from dripping into the wound. The liquid adhesive may adversely affect the healing of the wound if the adhesive runs into the wound. On the other hand, said liquid adhesive composition should not be so viscous as to make it difficult to dispense it from the container and/or apply it onto the skin. For medical applications, liquid adhesive compositions employed for example in wound closure or infection prevention, typically have a viscosity of less than 3,000 cps. More preferably such compositions have a viscosity of less than 2,000 cps. In a more preferred embodiment, the viscosity of such liquid adhesive compositions is in the range of from about 10 cps to about 1000 cps, preferably from about 20 cps to about 1000 cps and more preferably from about 40 cps to about 800 cps.

In preferred embodiments of the present invention, the liquid monomeric adhesive compositions may further contain small amounts of colorants such as dyes or pigments. Suitable dyes include derivatives of anthracene and other complex structures, specifically, without limitation, 1-hydroxy-4-[4-methylphenylamino]-9,10 anthracenedione (D&C violet No. 2); 9-(ocarboxyphenyl)-6-hydroxy-2,4,5,7-tetraiodo-3H-xanthen-3-one-, disodium salt, monohydrate (FD&C Red No. 3); disodium salt of 6-hydroxy-5-[(4-sulfophenyl)axo]-2-naphthalene-sulfonic acid (FD&C Yellow No. 6,); 2-(1,3 dihydro-3-oxo-5-sulfo-2H-indole-2-ylidine)-2,3-dihydro-3oxo-1H-ind-ole-5 sulfonic acid disodium salt (FD&C Blue No. 2); and 1,4-bis(4-methylanilino)anthracene-9,10-dione (D&C Green No. 6). The preferred dyes are D&C Violet No. 2, FD&C Blue No. 2, and D&C Green No. 6.

The liquid adhesive compositions of the instant invention may also optionally include preservatives. A preservative may be paraben such as alkyl parabens and salts thereof, ethylparaben, methylparaben, methylparaben sodium, propylparaben sodium, propylparaben, butylparaben, and the like. Other suitable preservatives include hydroquinone, pyrocatechol, resorcinol, 4-n-hexyl resorcinol, benzoic acid, benzyl alcohol, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, cresols, phenylmercuric compounds such as phenylmercuric borate, and phenylmercuric nitrate.

In embodiments of the present invention, the liquid monomeric adhesive compositions sterilized by X-ray irradiation may comprise an antimicrobial agent in an effective amount. The antimicrobial agents will be released from the polymer film of the adhesives formed on human or animal skins to inhibit microbial growth and prevent wound or surgical site infections. Suitable antimicrobial agents include antibacterial agents such as chlorhexidine and its salts, typical antibiotics, copolymers of vinylpyrrolidone and vinyl acetate, antiseptics, the iodine containing polymer such as povidone iodine, biguanidine compounds, phenol compounds such as 5-chloro-2-(2,4-dichlorophenoxy)phenol, acridine compounds, quaternary ammonium compounds such as benzalkonium chloride, cetylpridospores and zephiran, copolymers of vinylpyrrolidone and vinyl acetate cross-linked with polyisocyanates, heavy metal salts such as silver nitrate, and aldehyde compounds such as glutaraldhyde.

The liquid adhesive or microbial sealant compositions may be placed into and stored in any type of containers including, but not limited to plastic, aluminum and glass. Examples of containers include, but are not limited to, pouches, vials, applicators such as swabs or an applicator tip on a container holding liquid adhesive therein, ampoules, syringes, pipettes, and the like. In embodiments, the container enclosing the liquid monomeric adhesive or a microbial sealant composition is one of multi-layer construction of various materials.

In embodiments, the inner most layer in contact with the cyanoacrylate is composed of a nitrile polymer or copolymer. The multi-layer construction of the container may be any combination of any material suitable for storage and delivery of a liquid adhesive composition. By way of example, suitable materials include polymers, copolymers, thermoplastic polymers, plastics, nitrile polymers and copolymers, and metal, preferably foil.

Suitable thermoplastic polymers include the polyolefins, which include but are not limited to polyethylene (PE), and polypropylene (PP), and polyesters, such as, polyethylene terephthalate (PET). Any class of polyethylenes are suitable, including high density polyethylene (HDPE), high density cross-linked polyethylene (HDXLPE), cross-linked polyethylene (XLPE), medium density polyethylene (MDPE), linear low density polyethylene (LLDPE), low density polyethylene (LDPE), and very low density polyethylene (VLDPE), high molecular weight polyethylene (HMWPE), ultra low molecular weight polyethylene (ULMWPE) and ultra high molecular weight polyethylene (UHMWPE). Representative densities of certain polyethylenes are as follows: LDPE—0.910-0.925 g/cm$^3$; MDPE—0.926-0.940 g/cm$^3$; HDPE—0.941-0.965 g/cm$^3$. Other densities can be determined by the ordinary artisan by referencing ASTM D 1248 (1989). Preferred are homopolymers of polyethylene although suitable copolymers of vinyl acetate or acrylates may be used. Suitable polypropylenes are typically homopolymers, although random copolymer (PPCO) and block copolymers with other thermoplastic monomers may be used. Any commercially available packaging or film PET is suitable, including polyethylene terephthalate G copolymer (PETG) and oriented PET. Other suitable polymers include polycarbonate (PC), polyallomer (PA), polymethylpentene (PMP or TPX) polyketone (PK), polystyrene (PS), polyvinylchloride (PVC), naphthalate, polybutylene terphthalate, thermoplastic elastomer (TPE), mixtures thereof, and the like. Suitable nitrile polymers and copolymers include nitrile polymers produced by polymerizing a major proportion of a monounsaturated nitrile and a minor proportion of another monovinyl monomer or indene copolymerizable, nitrile polymers produced by polymerizing a major portion of a monounsaturated nitrile and a minor portion of another monovinyl monomer or indene copolymerizable therewith in the presence of a diene rubber, polyacarylates, polymethoactrylate, polyalkyl methacrylates, polyethers, polysiloxanes, polysulfones, polyphenylene sulfide, polyether ether ketones, thermoplastic polyimides, polybenzimidazoles, polyquinoxalones, polyoxazolines, styrene-acrylonitrile copolymer and acrylonitrile-butadiene-styrene copolymer, vinyl acetate containing polymers, maleic anhydride containing polymers, butadiene and/or isoprene based elastomers, acrylonitrile, and methacrylonitrile. Preferred are nitrile copolymers including preferably a copolymer of acrylonitrile and methyl acrylate, which is a product commercially available from BP America, BP Chemicals, Barex® Resin Division, Lima, Ohio, U.S.A. and is sold by the brand name "Barex®". Barex® resins are generally produced by the copolymerization of acrylonitrile and methyl acrylate in a 75:25 ratio onto a nitrile rubber backbone, which is used to provide impact strength. The refractive index of the nitrile rubber is matched to the polymer matrix in order to maintain transparency. The ISO abbreviation for Barex® resins is A/MA/B; its three main components being acrylonitrile, methyl acrylate, and butadiene.

The exceptional barrier properties offered by acrylonitrile copolymer make it an ideal inner layer material for use in construction of package bodies, in accordance with the present invention, to sterilize adhesive compositions using X-ray irradiation. The inner layer of acrylonitrile copolymer provides high barrier properties which ensure the stability of the liquid adhesive compositions stored therein. Acrylonitrile copolymer offers a high barrier to oxygen at all levels of relative humidity. This ensures that a consistently high barrier to oxygen is maintained, regardless of the humidity of the surrounding environment. In addition, the water vapor barrier properties of acrylonitrile copolymer are comparable to other plastic packaging materials and are ultimately enhanced by the outer layer secured thereto in accordance with the present invention. All of the properties of acrylonitrile copolymer enable it to be a suitable material as the package body for sterilizing cyanoacrylates via X-ray irradiation.

In certain embodiments, the container may be constructed such that the layers of materials may be any number of layers in any order, however it is important that the inner layer in contact with the liquid adhesive is a nitrile polymer or acrylonitrile copolymer.

In a preferred embodiment, the container comprises two parts, namely a top section and a bottom section, each comprising two or more layers, preferably two or three layers. Preferably the top section or front cover is one comprising three layers wherein the inner layer comprises a nitrile polymer, the middle layer comprises polypropylene and the outer layer comprises polyethylene or alternatively, the front cover may comprise an inner layer of nitrile polymer and an outer layer of polypropylene. Preferably, the bottom section or backing foil preferably also is one comprising three layers, preferably an inner layer of nitrile polymer, a middle layer of foil and an outer layer of polyethylene terephthalate. Alternatively, the bottom section is one comprising an inner layer of nitrile polymer and an outer layer of aluminum foil. The different layers of material may suitably have a thickness of from about 5 to about 1000 micrometers.

The container size may vary depending on the volume of liquid it contains. Containers of the invention may have a volume of about 0.1 ml to 10 ml, preferably about 0.2 ml to 8 ml, and more preferably about 0.3 ml to 8 ml. In order to inhibit premature polymerization, the volume of the container is preferably about 50 to 80 percent, preferably about 55 to 80 percent and more preferably 60 to 80 percent filled by the liquid monomer adhesive compositions.

Cyanoacrylate adhesive compositions in a suitable container such as, an applicator with an overpack can be sterilized by X-ray irradiation in different configurations. For example, cyanoacrylate-based compositions in a preferred container can be put into a unit box first and then stored in a second outer box for X-ray sterilization at different dosages. The unit box can include from about 2 to about 30 suitable containers with cyanoacrylate-based compositions, preferably from about 4 to about 25 suitable containers, and more preferably from about 5 to about 20 suitable containers. The outer box can include from about 3 to about 50 unit boxes, preferably from about 5 to about 40 unit boxes, and more preferably from about 5 to about 30 unit boxes. The density of the outer box typically can range from about 0.1 to about 0.6 $g/cm^3$, preferably from about 0.1 to 0.5 $g/cm^3$, and more preferably from about 0.15 to 0.45 $g/cm^3$.

In another embodiment, cyanoacrylate-based adhesive compositions can be sterilized by X-ray described herein in a box containing a large amount of suitable containers. The box can include from about 200 to about 4,000 suitable containers comprising cyanoacrylate adhesive compositions, preferably from about 300 to about 3,000 suitable containers, and more preferably from about 400 to 2,500 suitable containers. The density of the box containing a large amount of suitable container can range from about 0.04 to about 0.4 $g/cm^3$, preferably from about 0.05 to about 0.4 $g/cm^3$, and more preferably from about 0.05 to about 0.3 $g/cm^3$. A number of boxes including a large amount as described above of suitable containers with adhesive compositions can be placed in a carrier that is exposed to X-ray irradiation according to the present invention. For example, one carrier can hold from about 10 to about 50 boxes, preferably from about 10 to about 40 boxes, and more preferably from about 12 to about 40 boxes. This way, cyanoacrylate adhesive compositions can be sterilized on a large production scale, which makes the X-ray sterilization process quick and efficient with a shorter turnaround time compared to other irradiation sterilization techniques such as E-beam sterilization.

In preferred embodiments of the present invention, the container body may be wrapped with a secondary outer packaging. The secondary outer packaging may comprise any ethylene oxide permeable and compatible material, including but not limited to paper and plastics or a combination thereof. The secondary outer packaging may comprise a front wrapper and a back wrapper and may be constructed from medical grade paper. As an example, the back wrapper of the secondary packaging may be a medical grade paper coated with heat sealant, while the front wrapper may be a strong medical grade Kraft® paper coated with a low density polyethylene, which is compatible with radiation or ethylene oxide sterilization methods.

According to the embodiments of the present invention, the liquid adhesives may be bioabsorbable. The term bioabsorbable refers to polymers or medical devices that are able to be completely degraded, eroded, and/or gradually absorbed or eliminated by the body when such polymers or medical devices are exposed to body fluid such as blood. Bioabsorbable adhesives can be used in many different applications including but not limited to general wound closure, endoscopic surgery, cardiac surgery, hernia surgery, artheroscopic surgery. Preferred bioabsorbable adhesives of the present invention, include a mixtures of alkoxyalkyl cyanoacrylate and polyethylene glycol; and alkyl cyanoacrylate, alkoxyalkyl cyanoacrylate and polyethylene glycol. A preferred alkoxyalkyl cyanoacrylate is methoxyisopropyl cyanoacrylate. Other bioabsorbable adhesives may include copolymers of alkyl cyanoacrylate or alkoxyalkyl cyanoacrylate with other biocompatible monomers such as trimethylene carbonate, alkylene glycol, gylcolide, lactide, ε-caprolactone, and dioxane.

The following examples clearly demonstrate the overall nature and certain embodiments of the invention. These examples are intended to be illustrative only. The invention is not limited to the process parameters, materials and conditions in any way. Thus, the invention should in no way be construed as being limited to the following examples, but rather, should be construed to encompass any and all variations which become evident as a result of the teachings provided herein.

EXAMPLE 1

2-octyl cyanoacrylate monomer was stabilized with free radical and anionic polymerization inhibitors, to which 7.8 ppm of DC violet #2 was added. 81 lb of such 2-octyl cyanoacrylate composition was mixed with a trace amount of 18-crown-6 in a stainless steel container, equipped with the mechanical agitator, at room temperature. The bulk cyanocrylate composition was then packaged in a primary package or applicator with acrylonitrile copolymer as the inner layer and placed into a secondary package consisting of a plastic bubble package having a Tyvek® peel away backing. The cyanoacrylate composition contained in the primary and secondary packaging was then exposed to X-ray irradiation at doses of 6.96-8.59 kGy, 11.89-13.69 kGy and 15.25-18.88 kGy, respectively. The viscosities of this cyanoacrylate composition after X-ray sterilization were 6.54 cps, 6.54 cps and 7.36 cps, respectively, compared to 6.95 cps before X-ray sterilization.

EXAMPLE 2

Set times of the cyanoacrylate-based composition of Example 1 before and after X-ray sterilization were measured by using pig skin as the testing substrate. Pig skin (4×4 square inch) was prepared by wiping the surfaces of the skin with sterile gauze saturated with isopropanol. All oily substances were thereby removed from the pig skin. The surface was then wiped with sterile gauze to remove the isopropanol. The applicator containing cyanoacrylate was opened and adhesive was permitted to saturate the sponge applicator tip for about 10 seconds prior to application. A thin film was applied to the pig skin after which elapsed time was recorded by a stop watch. Set time was then recorded by stopping the clock when the film was dry as determined at the point where no liquid transfer occurred when the film was touched with a gloved finger. Table 2 shows the set time of composition contained in a preferred applicator after X-ray sterilization at three different dose ranges.

TABLE 2

Set time measurement of cyanoacrylate-based composition after X-ray sterilization at 6.96-8.59, 11.89-13.69 and 15.25-18.88 kGy.

| Treatment | Set Time (Second) | | | |
|---|---|---|---|---|
| | Test 1 | Test 2 | Test 3 | Average |
| Before sterilization | 10 | 8 | 11 | 9.7 |
| X-ray sterilization 6.96-8.59 kGy | 9 | 9 | 10 | 9.3 |
| X-ray sterilization 11.89-13.69 kGy | 10 | 12 | 9 | 10.3 |
| X-ray sterilization 15.25-18.88 kGy | 12 | 11 | 10 | 11.0 |

EXAMPLE 3

2-octyl cyanoacrylate monomer was stabilized with free radical and anionic polymerization inhibitors, to which 7.8 ppm of DC violet #2 was added. 844.6 g of such 2-octyl cyanoacrylate composition was then mixed with a trace amount of 18-crown-6 in a high density polyethylene bottle at room temperature for 3 hours. The bulk cyanocrylate composition was packaged in a preferred primary applicator with acrylonitrile copolymer as the inner layer and placed into a secondary package consisting of a plastic bubble and Tyvek paper. The cyanoacrylate composition contained in the applicator was then exposed to X-ray at dose range of 6.96-8.59 kGy. The viscosity of this cyanoacrylate composition after X-ray sterilization at 6.96-8.59 kGy is 7.77 cps compared to 7.56 cps before sterilization.

EXAMPLE 4

In a high density polyethylene bottle, 2-octyl cyanoacrylate was stabilized with both free radical and anionic stabilizers. 1994 g of such 2-octyl cyanoacrylate composition was mixed with a trace amount of 18-crown-6 and 7.8 ppm of DC Violet #2 at room temperature for 3 hours. The resulting composition was packaged in a preferred primary applicator with acrylonitrile copolymer as the inner layer and placed into a secondary package consisting of a plastic bubble and Tyvek paper. The cyanoacrylate composition contained in the applicator was then exposed to X-ray at dose range of 11.89-13.69 kGy. The viscosity of this cyanoacrylate composition after X-ray sterilization at 11.89-13.69 kGy is 7.36 cps compared to 6.74 cps before sterilization.

EXAMPLE 5

2-octyl cyanoacrylate monomer was stabilized with free radical and anionic polymerization inhibitors, to which 7.8 ppm of DC violet #2 was added. 3410 g of such 2-octyl cyanoacrylate composition was then mixed with a trace amount of 18-crown-6 in a high density polyethylene bottle at room temperature for 3 hours. The resulting composition was packaged in a preferred primary applicator with acrylonitrile copolymer as the inner layer and placed into a secondary package consisting of a plastic bubble and Tyvek paper. The cyanoacrylate composition contained in the applicator was then exposed to X-ray at a dose range of 15.25-18.88 kGy. The viscosity of this cyanoacrylate composition after X-ray sterilization at 15.25-18.88 kGy is 7.36 cps compared to 7.77 cps before sterilization.

EXAMPLE 6

The sterility of the cyanoacrylate compositions sterilized by X-ray irradiation at 6.96-8.59, 11.89-13.69 and 15.25-18.88 kGy was evaluated by the USP bacteriostasis and fungistasis testing using the direct transfer method. Test samples were immersed into 500 mL of Soybean Casein Digest Medium (SCDM) or Fluid Thioglycollate Medium (FTM). The test microorganism, such as *Bacillus subtilis, Candida albican*, or *Aspergillus niger*, was inoculated into each of the test sample containers and into a positive control container of the same medium at less than 100 colony forming units. All preparations were performed in an aseptic manner within a filtered clean bench. In order to obtain a quantitative measure of each microorganism, a duplicate plate count was performed. After inoculation, the test sample and positive control container were incubated in SCDM at 20-25° C. and in FTM at 30-35° C. for 14 days. Inoculated containers were observed periodically throughout the incubation period. Growth of the challenging microorganism was used to indicate the sterility. As shown in Table 6, no growth in both SCDM and FTM indicated that the test adhesive compositions after X-ray irradiation are sterile.

TABLE 6

Sterility results of cyanoacrylate-based composition in example 1 sterilized by X-ray irradiation at three different dose ranges

| Dose range | Sterility result | |
| --- | --- | --- |
| (kGy) | Growth in FTM | Growth in SCDM |
| 5.0-5.6 | No Growth | No Growth |
| 11.7-13.0 | No Growth | No Growth |
| 15.4-16.4 | No Growth | No Growth |

While the present invention has been described with an emphasis upon preferred embodiments, it will be obvious to those of ordinary skill in the art that variations in the preferred cyanoacrylate compositions and methods may be used and that it is intended that the invention may be practiced otherwise than as specifically described herein. Accordingly, the present invention includes all modifications encompassed within the spirit and scope of the invention as defined by the claims that follow.

What is claimed is:

1. A method for preparing a sterile, liquid monomeric cyanoacrylate adhesive composition in a sealed container using X-ray radiation, wherein the method comprises:
    (a) stabilizing a liquid monomeric cyanoacrylate adhesive composition using a combination of a free radical stabilizer and an anionic stabilizer to produce a stabilized liquid monomeric cyanoacrylate adhesive composition;
    (b) placing the stabilized liquid monomeric cyanoacrylate adhesive composition in a container and sealing said container; and
    (c) irradiating the stabilized liquid monomeric cyanoacrylate adhesive composition in said sealed container with X-ray radiation at a dose of from about 5 kGy to about 40 kGy, thereby producing a sterilized, stabilized liquid monomeric cyanoacrylate adhesive composition, wherein the sterilized, stabilized liquid monomeric cyanoacrylate adhesive composition exhibits no change in viscosity or a negligible change in viscosity after irradiation, and has a shelf life of at least two years at ambient temperature.

2. The method of claim 1 wherein the dose of X-ray radiation is from about 5 kGy to about 30 kGy.

3. The method of claim 2 wherein the dose of X-ray radiation is from about 5 kGy to about 25 kGy.

4. The method of claim 3 wherein the dose of X-ray radiation is from about 5 kGy to about 20 kGy.

5. The method of claim 1 wherein the liquid monomeric cyanoacrylate adhesive composition comprises a crown ether.

6. The method of claim 1 wherein the liquid monomeric cyanoacrylate adhesive composition comprises an alpha-cyanoacrylate monomer.

7. The method of claim 6 wherein the alpha-cyanoacrylate monomer is selected from the group consisting of: 2-octyl cyanoacrylate, dodecyl cyanoacrylate, 2-ethylhexyl cyanoacrylate, n-butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate, and mixtures thereof.

8. The method of claim 7 wherein the alpha-cyanoacrylate monomer is selected from the group consisting of: n-butyl cyanoacrylate, 2-octyl cyanoacrylate, and a mixture thereof.

9. The method of claim 1 wherein the container comprises an inner-most layer comprising a nitrile polymer.

10. The method of claim 1 further comprising the step of filtering the liquid monomeric cyanoacrylate adhesive composition through at least one filter under an inert and moisture-free atmosphere prior to the irradiation step, wherein the at least one filter has a pore size of from about 1 to about 200 µm.

11. A method for preparing a sterile, liquid monomeric cyanoacrylate adhesive composition in a sealed container using X-ray radiation, wherein the method comprises:
    (a) stabilizing a liquid monomeric cyanoacrylate adhesive composition with 2000 ppm to 8000 ppm of a free radical stabilizer selected from the group consisting of butylated hydroxy anisole (BHA), hydroquinone, catechol, hydroquinone monomethyl ether, butylated hydroxyanisol, 4-ethoxyphenol, 4-methoxyphenol, 3-methoxyphenol, 2-tert-butyl-4-methoxyphenol and 2,2-methylene-bis-(4-methyl-6-tert-butylphenol) and with either about 10 ppm to about 200 ppm of sulfur dioxide or about 5 ppm to about 50 ppm of a strong acid anionic stabilizer selected from the group consisting of perchloric acid, hydrochloric acid, hydrobromic acid, toluenesulfonic acid, fluorosulfonic acid, phosphoric acid, ortho-pohsphoric acid, meta-phosphoric acid, paraphosphoric acid, trichloroacetic acid, and sulfuric acid;
    (b) placing the stabilized liquid monomeric cyanoacrylate adhesive composition in a container and sealing said container; and
    (c) irradiating the stabilized liquid monomeric adhesive composition in said sealed container with X-ray radiation at a dose of from about 5 kGy to about 40 kGy, thereby producing a sterilized, stabilized liquid monomeric cyanoacrylate adhesive composition, wherein the sterilized, stabilized liquid monomeric cyanoacrylate adhesive composition exhibits no change in viscosity or a negligible change in viscosity after irradiation, and has a shelf life of at least two years at ambient temperature.

12. The method of claim 11 wherein the dose of X-ray radiation is from about 5 kGy to about 30 kGy.

13. The method of claim 12 wherein the dose of X-ray radiation is from about 5 kGy to about 25 kGy.

14. The method of claim 13 wherein the dose of X-ray radiation is from about 5 kGy to about 20 kGy.

15. The method of claim 11 wherein the liquid monomeric cyanoacrylate adhesive composition comprises an alpha-cyanoacrylate monomer.

16. The method of claim 15 wherein the alpha-cyanoacrylate monomer is selected from the group consisting of: 2-octyl cyanoacrylate, dodecyl cyanoacrylate, 2-ethylhexyl cyanoacrylate, n-butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate, and mixtures thereof.

17. The method of claim 16 wherein the alpha-cyanoacrylate monomer is selected from the group consisting of: n-butyl cyanoacrylate, 2-octyl cyanoacrylate, and a mixture thereof.

18. The method of claim 11 wherein the container comprises an inner-most layer comprising a nitrile polymer.

19. The method of claim 11 further comprising the step of filtering the liquid monomeric cyanoacrylate adhesive composition through at least one filter under an inert and moisture-free atmosphere prior to the irradiation step, wherein the at least one filter has a pore size of from about 1 to about 200 µm.

20. The method of claim 11 wherein the liquid monomeric cyanoacrylate adhesive composition comprises a crown ether.

* * * * *